(12) United States Patent
Collard

(10) Patent No.: US 8,961,612 B2
(45) Date of Patent: Feb. 24, 2015

(54) KNEE COMPONENT HAVING ORBITAL INTERFACE BOSS

(75) Inventor: Curt Collard, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/599,541

(22) Filed: Aug. 30, 2012

(65) Prior Publication Data

US 2014/0067077 A1    Mar. 6, 2014

(51) Int. Cl.
*A61F 2/38*    (2006.01)

(52) U.S. Cl.
CPC ........................................ *A61F 2/38* (2013.01)
USPC ........................................................ 623/20.15

(58) Field of Classification Search
CPC ............ A61B 17/1764; A61B 17/1675; A61F 2/3859; A61F 2/38; A61F 2/389; A61F 2220/0041; A61F 2002/2825; A61F 2002/30364; A61F 2002/30507; A61F 2002/30879
USPC ........................................... 623/20.14–20.36
See application file for complete search history.

(56) References Cited

U.S. PATENT DOCUMENTS

| | | |
|---|---|---|
| 4,790,852 A | 12/1988 | Noiles |
| 4,822,366 A | 4/1989 | Bolesky |
| 4,846,839 A | 7/1989 | Noiles |
| 5,133,760 A | 7/1992 | Petersen et al. |
| 5,137,535 A | 8/1992 | Keller |
| 5,147,406 A | 9/1992 | Houston et al. |
| 5,152,796 A | 10/1992 | Slamin |
| 5,152,797 A | 10/1992 | Luckman et al. |
| 5,194,066 A | 3/1993 | Van Zile |
| 5,290,313 A | 3/1994 | Heldreth |
| 5,370,593 A | 12/1994 | Wang |
| 5,387,240 A | 2/1995 | Pottenger et al. |
| 5,387,241 A | 2/1995 | Hayes |

(Continued)

FOREIGN PATENT DOCUMENTS

| | | |
|---|---|---|
| EP | 01004283 A2 | 5/2000 |
| EP | 1430856 A1 | 6/2004 |

(Continued)

OTHER PUBLICATIONS

Extended European Search Report for Application No. EP 13 18 2478 dated Oct. 21, 2013 (7 pages).

*Primary Examiner* — David Isabella
*Assistant Examiner* — Ann Schillinger
(74) *Attorney, Agent, or Firm* — Harness, Dickey

(57) ABSTRACT

A knee prosthesis constructed in accordance to the present disclosure includes a femoral component and a boss. The femoral component can have a first condylar portion and a second condylar portion connected by an inner condylar portion that defines an intercondylar recess, the inner condylar portion having a first engagement portion comprising a first plurality of engaging members extending therefrom. The boss can have a longitudinal body extending along a boss axis between first and second ends. The first end can be configured to selectively mate with a stem. The second end can include a second engagement portion comprising a second plurality of engaging members extending therefrom. The second engagement portion of the boss can be selectively coupled to the first engagement portion of the femoral component in a plurality of discrete positions to attain a corresponding plurality of angles of the boss axis relative to the femoral component.

19 Claims, 5 Drawing Sheets

(56) References Cited

U.S. PATENT DOCUMENTS

| | | | |
|---|---|---|---|
| 5,397,360 A | 3/1995 | Cohen et al. | |
| 5,405,395 A | 4/1995 | Coates | |
| 5,411,555 A | 5/1995 | Nieder | |
| 5,413,605 A | 5/1995 | Ashby et al. | |
| 5,413,607 A | 5/1995 | Engelbrecht et al. | |
| 5,458,637 A | 10/1995 | Hayes | |
| 5,549,689 A | 8/1996 | Epstein et al. | |
| 5,556,433 A | 9/1996 | Gabriel et al. | |
| 5,571,194 A | 11/1996 | Gabriel | |
| 5,653,764 A * | 8/1997 | Murphy | 623/23.15 |
| 5,755,805 A | 5/1998 | Whiteside | |
| 5,782,920 A | 7/1998 | Colleran | |
| 5,782,921 A | 7/1998 | Colleran et al. | |
| 5,824,097 A | 10/1998 | Gabriel et al. | |
| 5,876,459 A | 3/1999 | Powell | |
| 5,879,391 A * | 3/1999 | Slamin | 623/20.15 |
| 5,906,644 A | 5/1999 | Powell | |
| 5,951,603 A | 9/1999 | O'Neil et al. | |
| 6,010,534 A | 1/2000 | O'Neil et al. | |
| 6,071,311 A * | 6/2000 | O'Neil et al. | 623/20.15 |
| 6,074,424 A | 6/2000 | Perrone, Jr. et al. | |
| 6,099,569 A | 8/2000 | Keller | |
| 6,139,584 A | 10/2000 | Ochoa et al. | |
| 6,146,424 A | 11/2000 | Gray, Jr. et al. | |
| 6,423,096 B1 | 7/2002 | Musset et al. | |
| 6,436,145 B1 | 8/2002 | Miller | |
| 6,447,549 B1 | 9/2002 | Taft | |
| 6,485,519 B2 | 11/2002 | Meyers et al. | |
| 6,500,207 B1 | 12/2002 | Keller | |
| 6,527,807 B1 | 3/2003 | O'Neil et al. | |
| 6,669,728 B2 | 12/2003 | Despres, III et al. | |
| 6,682,568 B2 | 1/2004 | Despres, III et al. | |
| 6,719,800 B2 | 4/2004 | Meyers et al. | |
| 6,723,129 B2 | 4/2004 | Dwyer et al. | |
| 6,773,461 B2 | 8/2004 | Meyers et al. | |
| 6,866,683 B2 | 3/2005 | Gerbec et al. | |
| 6,869,447 B2 | 3/2005 | Lee et al. | |
| 6,887,276 B2 | 5/2005 | Gerbec et al. | |
| 6,896,702 B2 | 5/2005 | Collazo | |
| 6,953,479 B2 | 10/2005 | Carson et al. | |
| 7,125,193 B2 | 10/2006 | Despres, III et al. | |
| 7,544,211 B2 | 6/2009 | Rochetin | |
| 7,727,281 B2 * | 6/2010 | Ensign | 623/20.15 |
| 7,794,503 B2 | 9/2010 | Daniels et al. | |
| 2003/0065397 A1 | 4/2003 | Hanssen et al. | |
| 2004/0049285 A1 | 3/2004 | Haas | |
| 2004/0049286 A1 | 3/2004 | German et al. | |
| 2004/0117024 A1 | 6/2004 | Gerbec et al. | |
| 2004/0122521 A1 | 6/2004 | Lee et al. | |
| 2004/0162619 A1 | 8/2004 | Blaylock et al. | |
| 2008/0306603 A1 | 12/2008 | Reich et al. | |

FOREIGN PATENT DOCUMENTS

| | | |
|---|---|---|
| EP | 2042127 A1 | 4/2009 |
| WO | WO-9613233 A1 | 5/1996 |

\* cited by examiner

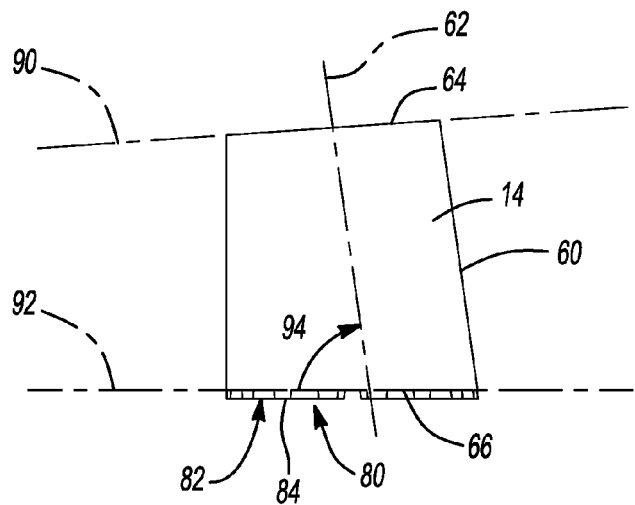
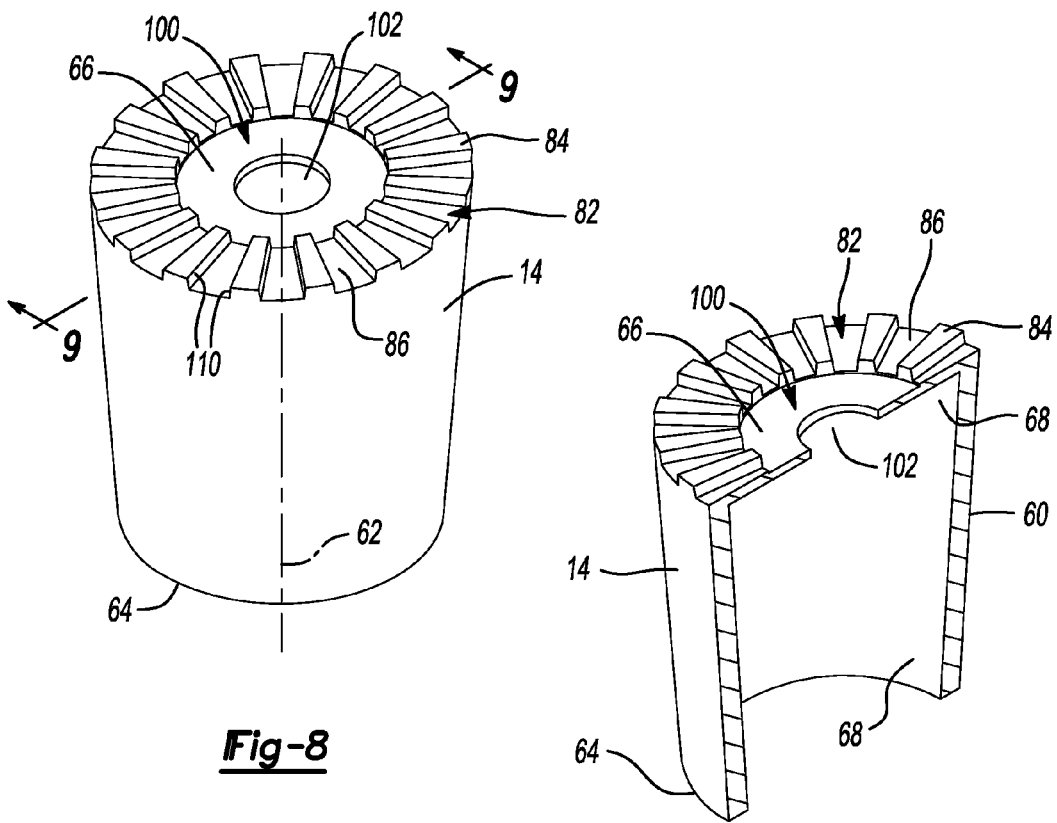

KNEE COMPONENT HAVING ORBITAL INTERFACE BOSS

FIELD

The present disclosure relates to knee prosthetic components and more specifically to an orbital interface boss that selectively mates with one of a femoral component and a tibial component.

BACKGROUND

This section provides background information related to the present disclosure which is not necessarily prior art.

A knee joint prosthesis typically comprises a femoral component and a tibial component. The femoral component and tibial component are designed to be surgically attached to the distal end of the femur and the proximal end of the tibia respectively. The femoral component is further designed to cooperate with the tibial component in simulating the articulating motion of an anatomical knee joint. Knee joint prostheses, in combination with ligaments and muscles, attempt to duplicate natural knee motion as well as absorb and control forces generated during the range of flexion.

While some knee joint prostheses have proven to be effective in replacing the anatomical knee joint, they nevertheless have several disadvantages. For example, knee joint prostheses sometimes lack adaptability to implant conveniently with a given patient. In this regard, in a normally shaped femur, the central canal is typically offset from the center of the femoral articulating surfaces. Furthermore, the central femoral canal may present various valgus angles from one patient to another.

While knee joint prosthesis having offset formal stems or femoral stems providing a range of valgus angles are known, they nevertheless can be subject to certain improvement.

SUMMARY

This section provides a general summary of the disclosure, and is not a comprehensive disclosure of its full scope or all of its features.

A knee prosthesis constructed in accordance to one example of the present disclosure includes a femoral component and a boss. The femoral component can have a first condylar portion and a second condylar portion connected by an inner condylar portion that defines an intercondylar recess. The inner condylar portion can have a first engagement portion comprising a first plurality of engaging members extending therefrom. The boss can have a longitudinal body extending along a boss axis between first and second ends. The first end can be configured to selectively mate with a stem. The second end can include a second engagement portion comprising a second plurality of engaging members extending therefrom. One of the first and second ends can define a non-orthogonal plane relative to the boss axis. The second engagement portion of the boss can be selectively coupled to the first engagement portion of the femoral component in a plurality of discrete positions to attain a corresponding plurality of angles of the boss axis relative to the femoral component. In other examples, a set of orbital bosses with many different non-orthogonal angles relative to the boss axis can be provided that would generate additional angle options. Therefore, boss angle and rotational angles provide multiple angle options.

According to additional features, the first plurality of engaging members can comprise a first set of teeth. The second plurality of engaging members can comprise a second set of teeth. The first and second sets of teeth can be configured to selectively interlock at a plurality of rotational orientations to attain a corresponding plurality of angular orientations relative to the femoral component. The second set of teeth can be arranged radially around a terminal end face of the second end of the boss. Each tooth of the second set of teeth can have opposite side surfaces that taper toward the boss axis.

According to additional features, the first and second ends can be arranged on the boss at non-orthogonal angles. The boss can define an aperture through the second end that is configured to selectively receive a fastener that mates with a stem extending from the first end of the boss. The inner condylar portion can define a passage that is configured to selectively receive the fastener.

A knee prosthesis can include a knee component having a first engagement portion having a first set of teeth extending therefrom. An indexing boss can have terminal end surfaces that are arranged along non-parallel planes. A first one of the terminal end surfaces can comprise a second set of teeth extending therefrom. The first and second sets of teeth can be configured to selectively interlock at a plurality of rotational orientations to attain a corresponding plurality of angular orientations relative to the knee component. Additionally, or alternatively, a plurality of indexing bosses can be provided having various angles.

According to additional features, the second set of teeth can be arranged radially around the first terminal end surface. The indexing boss can define an aperture that is configured to selectively receive a fastener that mates with a stem. The knee component according to one configuration is a femoral component. The knee component according to other configurations is a tibial component.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 7 is a side view of the orbital interface boss;

FIG. 8 is a perspective view of the orbital interface boss; and

FIG. 9 is a cross-sectional view taken along lines 9-9 of FIG. 8.

DETAILED DESCRIPTION

Example embodiments will now be described more fully with reference to the accompanying drawings.

Figure 1:
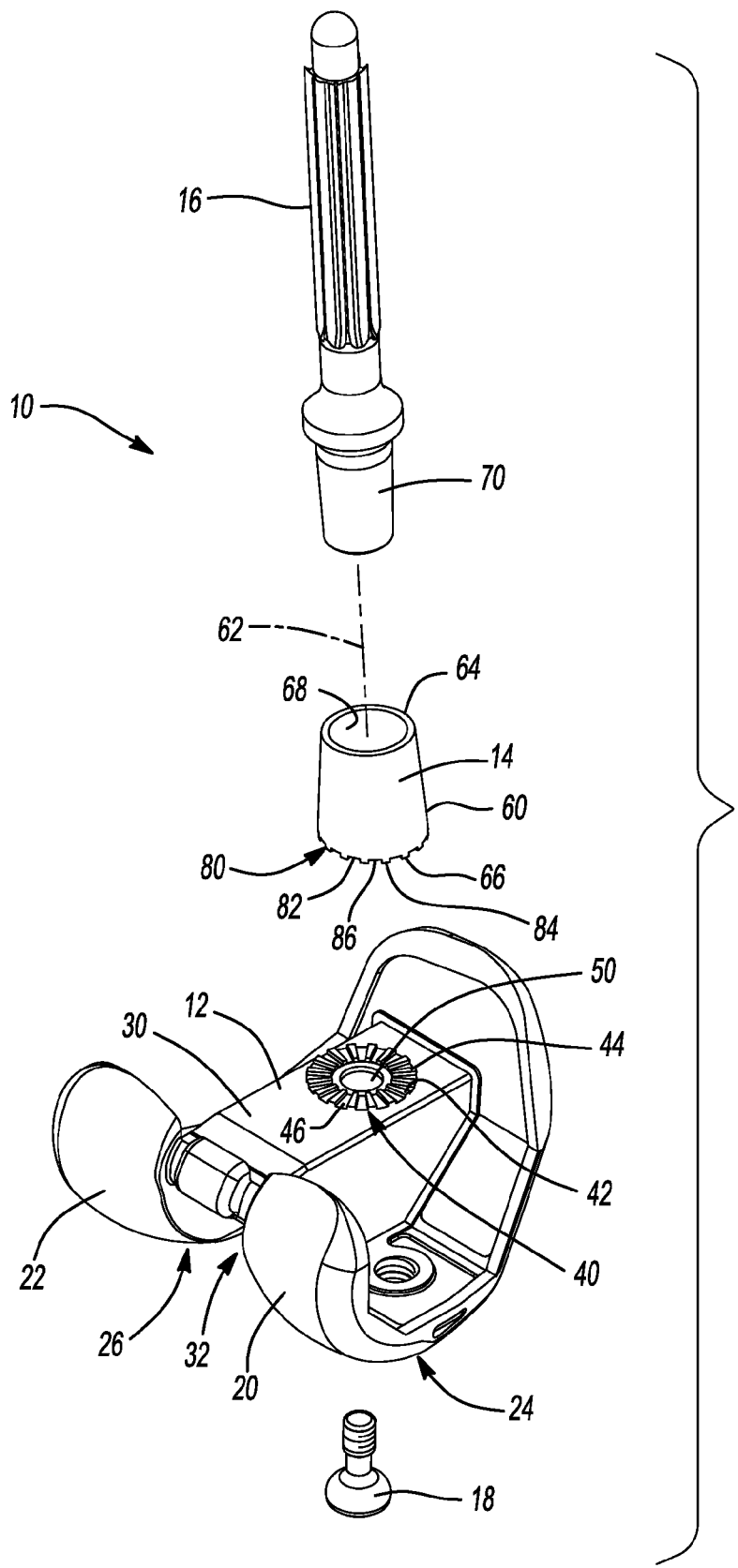
FIG. 1 is an exploded posterior perspective view of a femoral component and orbital interface boss constructed in accordance to one example of the present disclosure.
Figure 2:
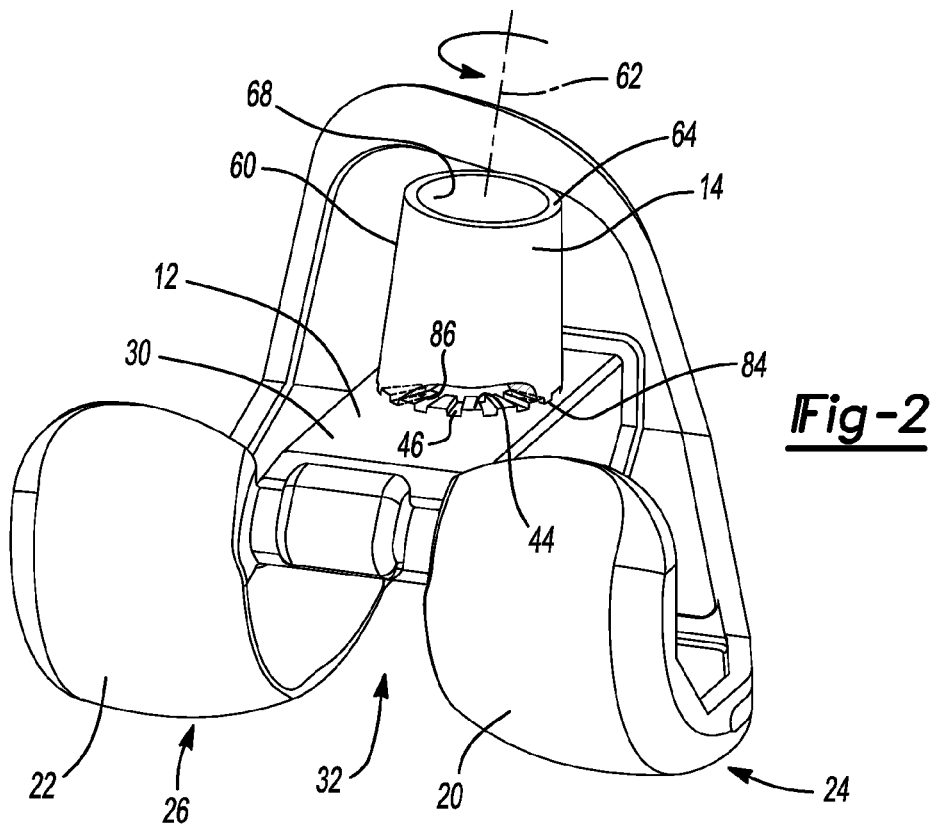
FIG. 2 is a posterior perspective view of the femoral component and orbital interface boss connected in a first orientation.
Figure 3:
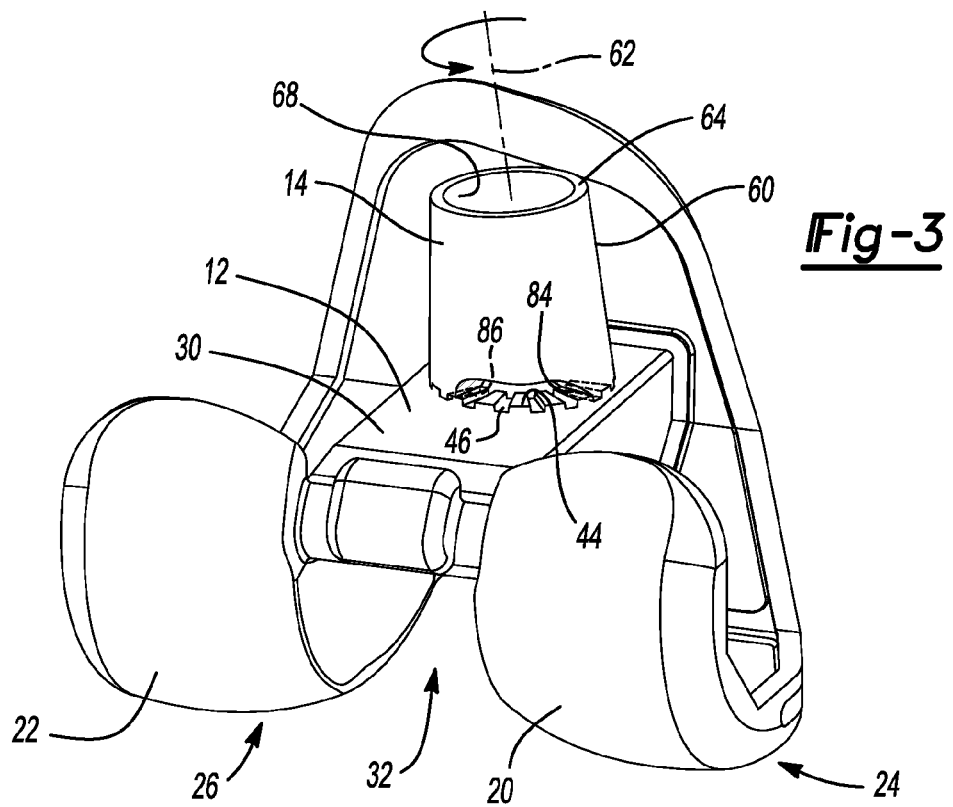
FIG. 3 is a posterior perspective view of the femoral component and orbital interface boss connected in a second orientation.

Referring initially to FIG. 1, a knee prosthesis constructed in accordance to one example of the present disclosure is shown and generally identified at reference numeral 10. The knee prosthesis 10 can generally include a femoral component 12, an indexing boss 14, a stem 16, and a fastener 18. The knee prosthesis 10 can incorporate one or more features of the commercially available VANGUARD® SSK Revision System and VANGUARD® 360 Revision System both of Biomet, Inc., located in Warsaw, Ind. In some examples, the knee prosthesis 10 can be a posterior stabilized knee prosthetic, however, it will be appreciated that the knee prosthesis can be of any suitable type without departing from the scope of the present disclosure. As will become appreciated from the following discussion, the indexing boss 14 can be selectively coupled relative to the femoral component 12 in a plurality of discrete positions to attain a desired varus/valgus angle relative to the femoral component 12 according to the particular needs of a given patient.

The femoral component 12 can include a first condylar portion 20 and a second condylar portion 22 that provide a first femoral bearing surface 24 and a second femoral bearing surface 26, respectively. The first and second condylar portions 20 and 22 of the femoral component 12 can be interconnected by an inner condylar portion or box 30 that defines an intercondylar recess 32. The inner condylar portion 30 can include a first engagement portion 40 having a first plurality of engaging members 42. In the particular example shown, the first plurality of engaging members 42 comprise a first set of teeth 44 and a corresponding first set of valleys 46. As will become appreciated from the following discussion, the geometrical configuration of the teeth 44 is exemplary. In this regard, teeth having other geometries will be incorporated. The inner condylar portion 30 can define a passage 50 for selectively accommodating the fastener 18 when coupling to the stem 16.

With continued reference to FIG. 1 and additional reference to FIGS. 7-9, the boss 14 can generally comprise a longitudinal body 60 extending along a boss axis 62 between a first end 64 and a second end 66. In the example shown, the first end 64 can include a female tapered receiving portion 68 configured to cooperatively receive a complementary male extending portion 70 formed on the stem 16. The second end 66 can include a second engaging portion 80 having a second plurality of engaging members 82. In the example shown, the second plurality of engaging members 82 can include a second series of teeth 84 and a corresponding second series of valleys 86. The teeth 84 can be configured with a geometry that is complementary to the first set of teeth 44 provided on the first engagement portion 40. In this regard, the second set of teeth 84 can be configured to cooperatively and discretely index around the first set of teeth 44 on the femoral component 12. The term "index" is used to denote cooperative interlocking of the first set of teeth 44 into the respective second set of valleys 86 and the second set of teeth 84 into the respective first set of valleys 46 during rotatable motion of the boss 14 around the boss axis 62. Once the desired angle is attained, the fastener can be inserted through the passage 50 and secured to the male extending portion 70 of the stem 16 to fix the boss 14 to the femoral component 12.

With particular reference now to FIG. 7, the first end 64 of the boss 14 extends along a first plane 90. The second end 66 of the boss 14 extends along a second plane 92. The first plane 90 and the second plane 92 can extend along intersecting planes. In this regard, the axis 62 can define an angle 94 that is non-orthogonal relative to the second plane 92. As can be appreciated, by rotatably indexing the second end 66 of the boss 14 around the first set of teeth 44 on the femoral component 12, a surgeon can attain a plurality of discrete angles between the boss axis 62 and the femoral component 12. Therefore, a surgeon can selectively determine and fix the boss 14 relative to the femoral component 12 in a preferred orientation. In some examples, a set of orbital bosses may be provided that offer distinct angles 94. In this regard, a surgeon may select an orbital boss having an angle 94 that satisfies the need of a particular patient.

With particular reference to FIG. 8, the second end 66 of the boss 14 can provide a terminal end face 100 that defines an aperture 102 therethrough. The second set of teeth 84 can be arranged generally radially around the terminal end face 100 of the second end 66. Each tooth 84 can include opposite side surfaces 110 that taper toward the boss axis 62.

Figure 4:
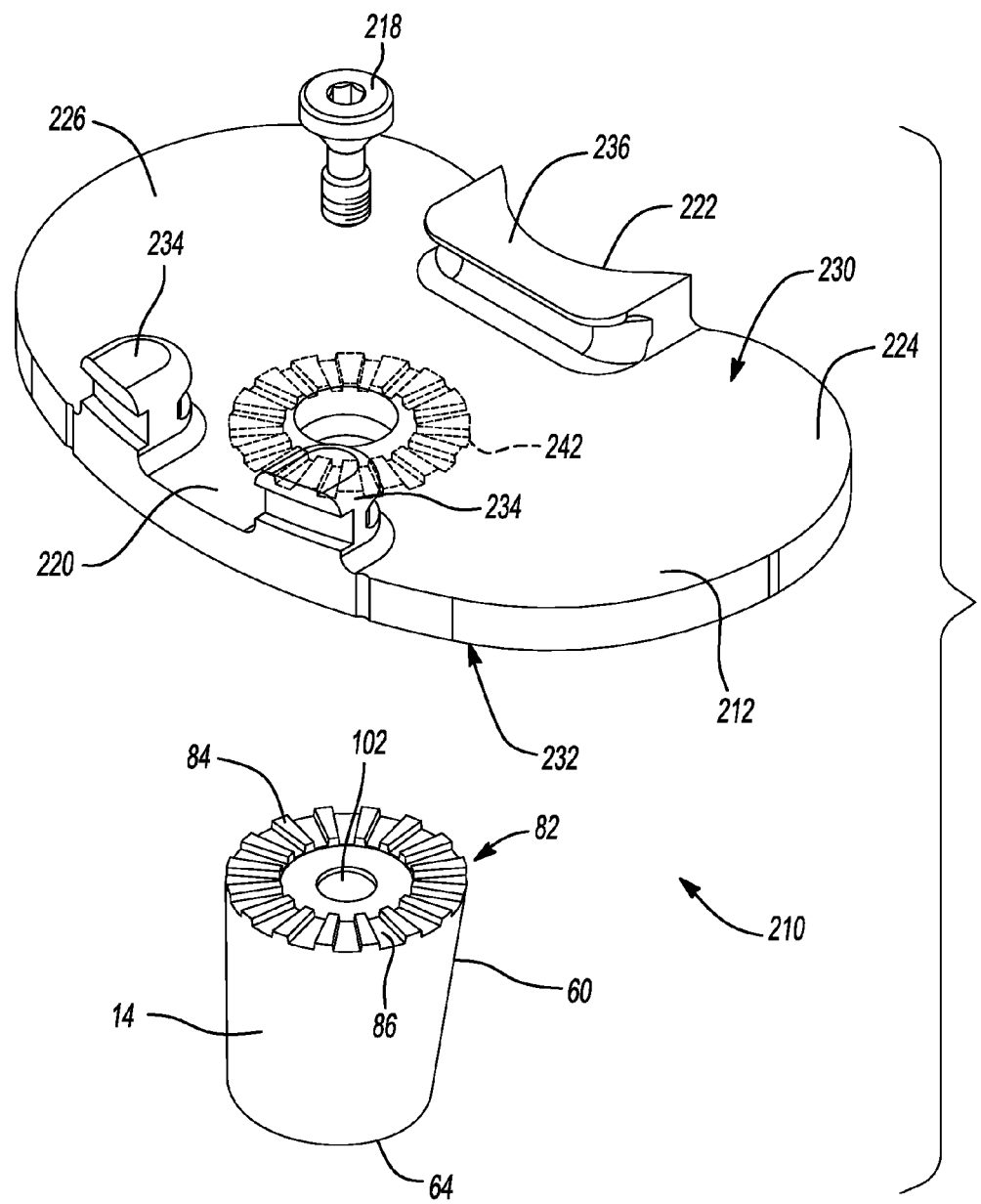
FIG. 4 is an exploded anterior perspective view of a tibial component and orbital interface boss.
Figure 5:
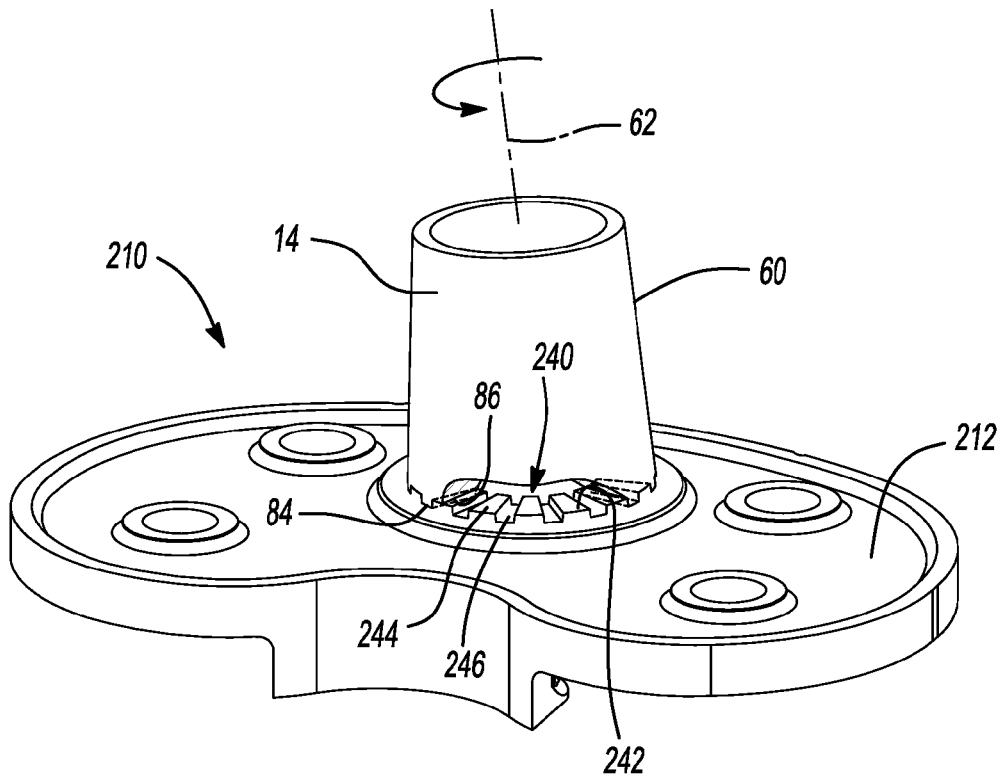
FIG. 5 is a posterior perspective view of the tibial tray and orbital interface boss connected in a first orientation.
Figure 6:
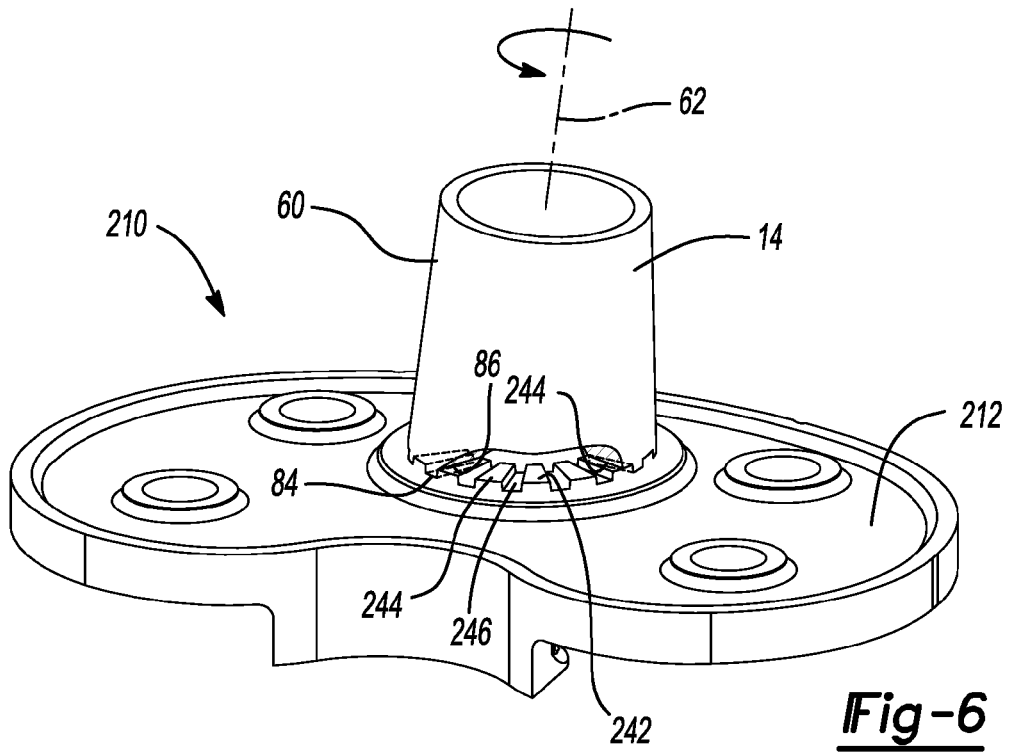
FIG. 6 is a posterior perspective view of the tibial tray and orbital interface boss connected in a second orientation.

Referring now to FIGS. 4-6, a knee prosthesis 210 constructed in accordance to additional features of the present disclosure will be described. The knee prosthesis 210 can generally include a tibial component 212, a tapered head fastener 218, and the boss 14. As can be appreciated, the boss 14 can be configured for use with either of the femoral component 12 of the knee prosthesis 10 (FIG. 1) or the tibial component 212 of the knee prosthesis 210. The tibial component 212 can generally include an anterior portion 220, a posterior portion 222, a medial portion 224, and a lateral portion 226. The tibial component 212 can include a superior bearing engaging surface 230 and an inferior bone engaging surface 232. The exemplary tibial component 212 can further include a pair of integrally formed posts 234 which extend superiorly at the anterior portion 220. A catch 236 can also be provided at the posterior portion 222. The posts 234 can be configured to cooperate with a locking bar (not specifically shown) to secure a tibial bearing such as disclosed in commonly owned U.S. Pat. No. 8,187,280, which is expressly incorporated herein by reference. In this regard, the posts 234 and the catch 236 can be used to secure a tibial bearing to the tibial component 212. It is appreciated that other retaining features may be employed for securing a tibial bearing to the tibial component 212. Likewise, it is appreciated that the tibial component 212 may alternatively be adapted for use with a floating bearing. In such an example, the superior surface 230 may be highly polished to provide a substantially smooth tibial bearing surface. While not specifically shown, a floating bearing having a substantially planar inferior bearing surface may be located above the tibial component 212. In this way, the floating bearing may slidably move relative to the highly polished superior surface 230 of the tibial component 212.

As shown in FIGS. 5 and 6, the tibial component 212 can include a third engagement portion 240 having a third plurality of engaging members 242. In the example shown, the third plurality of engaging members 242 can include a third series of teeth 244 and a corresponding third set of valleys 246. As shown in FIGS. 5 and 6, the boss 14 can be rotatably indexed relative to the third engagement portion 240 until a desired angle of the boss axis 62 relative to the tibial component 212 is attained. Specifically, the boss 14 can be rotated around the axis 62 until a desired angle is attained relative to the tibial component 212. Once the desired angle is attained, the first set of teeth 44 are nestingly received into the third set of valleys 246. Similarly, the third series of teeth 244 are nestingly received into the first set of valleys 46. When the desired angle is attained, a surgeon can secure the fastener 218 to the boss 14 to fix the boss 14 to the tibial component 212. Again, it will be appreciated that a set of orbital bosses may be provided having various angles.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A knee prosthesis comprising:
a femoral component having a first condylar portion and a second condylar portion connected by an inner condylar portion that defines an intercondylar recess, the inner condylar portion having a first engagement portion comprising a first plurality of engaging members extending therefrom; and
a boss having a longitudinal body extending along a boss axis between first and second ends, the first end configured to selectively mate with a stem and the second end including a second engagement portion comprising a second plurality of engaging members extending therefrom, wherein one of the first and second ends defines a non-orthogonal plane relative to the boss axis such that when the second engagement portion of the boss is coupled to the first engagement portion of the femoral component the boss axis relative to the femoral component will vary based on rotational orientation of the second engagement portion of the boss with respect to the first engagement portion of the femoral component.

2. The knee prosthesis of claim 1 wherein the first plurality of engaging members comprises a first set of teeth.

3. The knee prosthesis of claim 2 wherein the second plurality of engaging members comprises a second set of teeth.

4. The knee prosthesis of claim 3 wherein the first and second sets of teeth are configured to selectively interlock at a plurality of rotational orientations to attain a corresponding plurality of angular orientations relative to the femoral component.

5. The knee prosthesis of claim 4 wherein the second set of teeth is arranged radially around a terminal end face of the second end of the boss.

6. The knee prosthesis of claim 5 wherein each tooth of the second set of teeth has opposite side surfaces that taper toward the boss axis.

7. The knee prosthesis of claim 4 wherein the first and second ends are arranged on the boss at non-orthogonal angles.

8. The knee prosthesis of claim 7 wherein the boss defines an aperture through the second end that is configured to selectively receive a fastener that mates with a stem extending from the first end of the boss.

9. The knee prosthesis of claim 8 wherein the inner condylar portion defines a passage that is configured to selectively receive the fastener.

10. A knee prosthesis comprising:
a knee component having a first engagement portion including a first set of teeth extending therefrom; and
an indexing boss having terminal end surfaces that are arranged along non-parallel planes, wherein a first one of the terminal end surfaces comprises a second set of teeth extending therefrom, wherein the first and second sets of teeth are configured to selectively interlock at a plurality of rotational orientations to attain a corresponding plurality of angular orientations relative to the knee component due to the terminal end surfaces being arranged along non-parallel planes.

11. The knee prosthesis of claim 10 wherein the second set of teeth are arranged radially around the first terminal end surface.

12. The knee prosthesis of claim 11 wherein the indexing boss defines an aperture that is configured to selectively receive a fastener that mates with a stem.

13. The knee prosthesis of claim 10 wherein the knee component comprises a femoral component.

14. The knee prosthesis of claim 10 wherein the knee component comprises a tibial component.

15. A knee prosthesis comprising:
a knee component having a first engagement portion including a first set of teeth and valleys radially arranged thereon; and
an indexing boss having terminal end surfaces that are arranged along non-parallel planes, wherein a first one of the terminal end surfaces comprises a second set of teeth and valleys radially arranged thereon, wherein the first and second sets of teeth are configured to selectively interlock with corresponding second and first sets of valleys, respectively at a plurality of rotational orientations to attain a corresponding plurality of angular orientations of the indexing boss relative to the knee component due to the terminal end surfaces of the indexing boss being arranged along non-parallel planes.

16. The knee prosthesis of claim 15 wherein the indexing boss defines an aperture that is configured to selectively receive a fastener that mates with a stem.

17. The knee prosthesis of claim 16 wherein each tooth of the second set of teeth has opposite side surfaces that taper toward the boss aperture.

18. The knee prosthesis of claim 15 wherein the knee component comprises a femoral component.

19. The knee prosthesis of claim 15 wherein the knee component comprises a tibial component.

* * * * *